(12) United States Patent
Bruno-Blanch et al.

(10) Patent No.: US 7,763,650 B2
(45) Date of Patent: Jul. 27, 2010

(54) PHARMACEUTICAL COMPOUND AND METHOD

(75) Inventors: Luis Bruno-Blanch, La Plata (AR); Sung Chin Moon, La Plata (AR)

(73) Assignees: Medipharma S.A., Buenos Aires, La Plata (AR); University Nacional De La Plata, La Plata, Buenos Aires (AR)

( * ) Notice: Subject to any disclaimer, the term of this patent is extended or adjusted under 35 U.S.C. 154(b) by 1009 days.

(21) Appl. No.: 11/375,936

(22) Filed: Mar. 15, 2006

(65) Prior Publication Data

US 2007/0219164 A1 Sep. 20, 2007

(51) Int. Cl.
- *A61K 31/36* (2006.01)
- *A61K 31/19* (2006.01)
- *C07C 69/76* (2006.01)
- *C07C 69/95* (2006.01)
- *C07D 325/00* (2006.01)

(52) U.S. Cl. .................. 514/465; 514/557; 560/53; 560/54; 549/32

(58) Field of Classification Search .......... 558/70, 558/89, 120, 160; 514/102, 465, 557; 560/53, 560/54; 549/32
See application file for complete search history.

(56) References Cited

U.S. PATENT DOCUMENTS

| | | | |
|---|---|---|---|
| 4,595,695 A | 6/1986 | Ladkani et al. | 514/512 |
| 5,763,392 A | 6/1998 | Hansen et al. | 514/2 |
| 2006/0106000 A1* | 5/2006 | Nicolau et al. | 514/102 |
| 2009/0029951 A1* | 1/2009 | Nicolau et al. | 514/143 |

FOREIGN PATENT DOCUMENTS

| | | | |
|---|---|---|---|
| JP | 0208690 | * | 3/1990 |
| JP | 082084407 | * | 8/1996 |
| WO | 9621440 | * | 7/1996 |

OTHER PUBLICATIONS

Van Calker et al., Effect of Lithium ions on the Metabolism of Phosphoinositides, Studies with Rat Pheochromocytoma Cells (PC-12 cells). Dept of Psychiatry, Univ. of Munich, Munich Fed. Rep. of Germany; Pharmacopsychiatry, 1986, 19(4), 276-277.*
Sureshan et al., Topochemical Transketalization Reaction Driven by Hydrogen Bonding; Jour. of American Chemical Society; 2004, 126(30), 9174-9175.*
N. Bodor et al.; "Synthesis and Pharmacological Evaluation of Prodrugs of Valproic Acid"; Pharmazie, vol. 55, No. 3, 2000, pp. 184-186.

* cited by examiner

*Primary Examiner*—James O Wilson
*Assistant Examiner*—Ebenezer Sackey
(74) *Attorney, Agent, or Firm*—Norris, McLaughlin & Marcus

(57) ABSTRACT

A new pharmaceutical compound for treating central nervous disorders, the compound comprising a therapeutically effective amount of valproic acid or pharmaceutically acceptable derivative thereof covalently bonded to myo-inositol. The invention also provides a composition, method for treating a patient and a method for obtaining the compound.

9 Claims, No Drawings

PHARMACEUTICAL COMPOUND AND METHOD

BACKGROUND OF THE INVENTION

1. Field of the Invention

The present invention relates to a new compound for treating central nervous disorders and more particularly the invention refers to a compound comprising valproic acid or any derivative thereof covalently bound to myo-inositol, wherein the therapeutic activity of compound combining valproic acid and myo-inositol is increased several times as compared to the specific therapeutic activity of the valproic acid alone.

2. Description of the Prior Art

Central nervous disorders comprise several affections like epilepsy, bipolar disorders and migraine, and affect an import part of a population particularly insofar as to migraine and bipolar disorders is concerned. Bipolar disorders are those related to affective disorders and more particularly to changes in mood and disturbances concerning depression and mania. While mania involves excessive exuberance and enthusiasm, depression, on the opposite, involves apathy and low self-esteem, among other symptoms. There are individuals that are affected by both depression and mania and this disorder is known as bipolar disorder. Unipolar disorder is that one involving only one of both affections mentioned before.

While anti-depressants are effective for treating unipolar depression these drugs are not effective for mania. Valproic acid a relatively new anti-epileptic drug has demonstrated to be effective in treatment of mania in bipolar depression. However, valproic acid has different drawbacks and disadvantages, one of them is the short half life time, therefore, a dose must be administered to a patient several times a day to prevent the drug fluctuations of plasma concentrations. In addition, therapeutic doses of valproic acid and several of its derivatives are toxic and provide side effects, such as nausea, dizziness, etc. in many patients.

As disclosed in U.S. Pat. No. 4,595,695, a prodrug of valproic acid comprising 2-propylpentanoil-di-n-propyl acetate has been developed to prevent the above disadvantages however this ester prodrug has proved to be toxic to animals and as anti-epileptic and psychotic drug has not been effective. In addition, this prodrug has low bioavailability and slow absorption.

On the other hand, myo-inositol is known in the nutritional field to be an important nutritional component of the diet. U.S. Pat. No. 5,763,392 to Hansen et al. discloses the use of myo-inositol as an effective plasma glucose lowering agent. Myo-inositol is the major nutritionally active form of inositol, is vital to many biological processes of the body, participating in a diverse range of activities. Myo-inositol is one of nine distinct isomers of inositol. It is essential for the growth of rodents, but not for most animals, including humans. Humans can make myo-inositol endogenously, which they do from glucose, and, even though myo-inositol is sometimes referred to as a vitamin, it is not a vitamin for humans or most animals. However, the dietary intake of myo-inositol can influence the levels of circulating and bound myo-inositol in the body and may influence certain biological activities. Nutritional supplementation of this cyclitol may affect behavior and may have anti-depressant and anti-anxiety activities.

Myo-inositol is also known as inositol, hexahydroxycyclohexane, cyclohexanehexol, and, chemically, as cis-1,2,3,5-trans-4,6-cyclohexanehexol The mechanism of action of myo-inositol has yet to be fully elucidated. However, much is known about the biological roles of myo-inositol and some speculation can be made. Myo-inositol is metabolized to phosphatidylinositol, which makes up a small, but very significant, component of cell membranes.

Phosphatidylinositol can be converted to phosphatidylinositol-4,5-bisphosphate, a key intermediate in biological signaling. Phosphatidylinositol-4,5-bisphosphate is the precursor of at least three second-messenger molecules. These are inositol-1,4,5-triphosphate, which modifies intracellular calcium levels, diacylglycerol, which regulates some members of the protein kinase C family, and phosphatidylinositol-3,4,5-triphosphate, which is involved in signal transduction.

Some of the second-messenger activity is related to activation of serotonin receptors. It is hypothesized that the mechanism of action of myo-inositol's possible benefit in the management of depression, panic attacks and obsessive-compulsive behavior may be explained by myo-inositol's role as a second-messenger precursor.

Myo-inositol is absorbed from the small intestine following ingestion and is transported by the portal circulation to the liver and then by the systemic circulation to various tissues in the body, including the brain. Myo-inositol crosses the blood-brain barrier.

Within the liver and the various tissues of the body, myo-inositol enters into a wide range of diverse biochemical pathways. Myo-inositol reacts with CDP-diacylglycerol to form the phospholipid phosphatidylinositol, which can be incorporated into membrane structure. Phosphatidylinositol, via kinase reactions, forms phosphatidyl-4,5-bisphosphate, which is the precursor to inositol-1,4,5-triphosphate, diacylglycerol, phosphatidylinositol-3,4,5-triphosphate, myo-inositol 1,3,4-triphosphate and myo-inositol 1,3,4,5-tetrakisphosphate, among others. The myo-inositol phosphates can be dephosphorylated via phosphatases.

Considering the several drawbacks of the valproic acid some modified drugs have been made with the aim of overcoming the undesirable side effects and the disadvantageous physical and pharmacokinetic of the drug, however those drug modifications, while improved the drugs characteristics, have a less potent therapeutic effect.

In an attempt to prolong the effect of valproic acid the concept of prodrug which will be biotransformed almost completely to valproic acid in a rate limiting fashion has been tried, so far without success. This drug is 2-propylpentanol-di-n-propyl acetate. However this ester has proved to be very toxic to animals and was not introduced for therapy.

The novel compounds according to the present invention are myo-inositol ester prodrugs of an acid. Other such esters, serving as prodrugs are already in therapeutic use. For example 1'-ethoxycarbonyloxyethyl ester prodrugs of the penicillin series such as, for example, .alpha.-aminopenicillins and penicillin G are known.

It has also been found that the absorption of such esters from the intestinal tract is superior to the absorption of the corresponding free acids, which means that upon oral administration they yield higher blood concentrations than the corresponding free acid of .alpha.-aminopenicillin.

Usually the unionized form of a drug is absorbed more efficiently than its ionic species. In the case of valproic acid, the carboxylic group is significantly ionized at physiological pH. The result is that valproic acid is poorly absorbed through lipid-water membrane barriers, and in addition to the prodrugs and esters of valproic acid is very important to find ways to reduce the bounds to plasmatic proteins.

In view of the foregoing it would be very desirable to find a new compound based on valproic acid that, in combination with the benefits of myo-inositol, is effective in the treatment of central nervous disorders, such as bipolar disorders, and with reduced doses of the associated drugs in order to reduce side effects and toxicity.

SUMMARY OF THE INVENTION

It is therefore one object of the present invention to provide a new compound comprising a therapeutically effective amount of valproic acid, or any pharmaceutically acceptable derivative thereof covalently bonded to an effective amount of myo-inositol, with the result that the compound has a higher therapeutic effect as compared to valproic acid alone and, therefore, less number of doses must be administered to get the same therapeutic result.

It is still another object of the present invention to provide a compound comprising valproic acid and myo-inositol and the esters thereof, including mono-, di-, tri-, tetra-, penta- and hexa-2-(propylpentanoil)myo-inositol, the salts thereof and all the intermediate compounds formed with the several protecting groups hydroxyl, as well as all the chirality and position isomers thereof.

Except (±)3,6-di-O-valproil-1,2:4,5-di-O-isopropylidenmyo-inositol, (±)3,6-di-O-valproil-4,5-O-isopropylidenmyo-inositol and (±)3,6-di-O-valproil-myo-inositol It is even another object of the present invention to provide a partial and/or total removal of the protective groups, the partial and/or total hydrolysis of the esters of valproic acid with or without the protective groups for preparing all the myo-inositol isomers, 63 regioisomers, with 15 meso forms and 24 pairs of enantiomers.

It is still another object of the present invention to provide a compound of the formula:

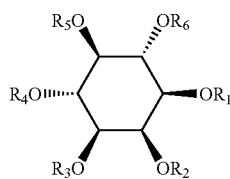

wherein:
$R_1$, $R_2$, $R_3$, $R_4$, $R_5$ and $R_6$ is each independently selected from the group consisting of H; 2-propylpentanoyl; O-cyclohexyl-O; O-isopropylidene and $PO_3H_2$;
with the proviso:
when $R_1$=2-propylpentanoyl, then $R_2$=$R_3$=$R_4$=$R_5$=$R_6$=2-propylpentanoyl;
when $R_1$-$R_2$=$R_5$-$R_6$=di-O-isopropylidene then $R_3$-$R_4$=2-propylpentanoyl;
when $R_1$=$R_2$=$R_3$=$R_4$=$PO_3H_2$ then $R_5$=$R_6$=2-propylpentanoyl or other positions in different groups;
when $R_1$=$R_2$=$R_3$=$R_4$=O-cyclohexyl-O then $R_5$=$R_6$=2-propylpentanoyl;
when $R_1$=$R_2$=O-isopropylidene then $R_3$=$R_4$=$R_5$=$R_6$=2-propylpentanoyl;
when $R_1$=$R_2$=H then $R_3$=$R_4$=$R_5$=$R_6$=2-propylpentanoyl;
when $R_1$=$R_2$=$R_5$=$R_6$=H then $R_3$=$R_4$=2-propylpentanoyl;
including the isomers, esters, protectors and salts thereof.

It is even another object of the present invention to provide a pharmaceutical composition comprising a therapeutically effective amount of valproic acid or pharmaceutically acceptable derivative thereof covalently bonded to a moiety of myo-inositol; and a pharmaceutically acceptable carrier.

It is a further object of the present invention to provide a method for treating a central nervous disorder in a subject, such as epilepsy, migraine, bipolar disorder, the method comprising the step of administering to the subject a therapeutically effective amount of valproic acid or pharmaceutically acceptable derivative thereof covalently bonded to a moiety of myo-inositol; and a pharmaceutically acceptable carrier.

It is a further object of the present invention to provide a process for preparing a pharmaceutical compound which comprises:
a) reacting a myo-inositol based compound with a valproic acid based compound into a solution, and
b) collecting a reaction product.

DESCRIPTION OF THE PREFERRED EMBODIMENTS

The present invention relates to some novel and useful myo-inositol ester prodrugs of valproic acid, a process for its production and of an anti-epileptic pharmaceutical preparation comprising such esters with less ulcerogenicity when administered orally than is valproic acid from which it is derived. This novel esters acts as prodrugs exhibiting characteristics of a slow release profile of the parent drug valproic acid, from which it is derived, and is suitable for the satisfactory control of the epileptic patient.

Disclosed is a new compound comprising the combination of valproic acid of the formula:

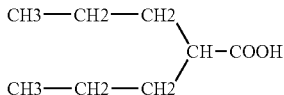

and myo-inositol having the formula:

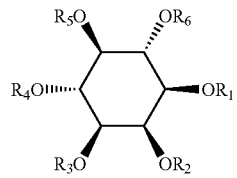

wherein R is H.
The inventive compound is obtained by reacting the valproic acid (in a reacting form, like valproyl chloride, anhydride, in the presence of a catalyst like piridine, trietilamine, 4-dimetiypiridine, 4-pirrolidinpiridine and others) with the myo-inositol and, more particularly the compound has the formula I:

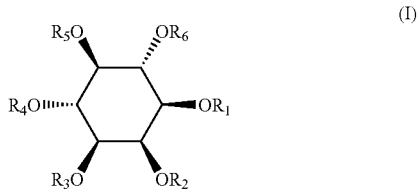

wherein:
$R_1$, $R_2$, $R_3$, $R_4$, $R_5$ and $R_6$ is each independently selected from the group consisting of H; 2-propylpentanoyl; O-cyclohexyl-O; O-isopropylidene and $PO_3H_2$; etc with the proviso:
when $R_1$=$R_2$=$R_3$=$R_4$=$R_5$=$R_6$=2-propylpentanoyl;
when $R_1$-$R_2$=$R_5$-$R_6$=di-O-isopropylidene then $R_3$-$R_4$=2-propylpentanoyl;

when $R_1=R_2=R_3=R_4=PO_3H_2$ then $R_5=R_6=$2-propylpentanoyl or other positions in different groups;

when $R_1=R_2=R_3=R_4=$O-cyclohexyl-O then $R_5=R_6=$2-propylpentanoyl;

when $R_1=R_2=$O-isopropylidene then $R_3=R_4=R_5=R_6=$2-propylpentanoyl;

when $R_1=R_2=$H then $R_3=R_4=R_5=R_6=$2-propylpentanoyl;

when $R_1=R_2=R_4=R_5=$H then $R_3=R_6=$2-propylpentanoyl;

when $R_1=R_2=R_5=R_6=$H then $R_3=R_4=$2-propylpentanoyl.

The compound also includes the isomers, pure optical products and racemic mixtures, esters, protectors and salts thereof, and the compound is preferably for treating central nervous disorders such as epilepsy, bipolar disorders, convulsions and migraine.

The invention comprises the synthesis of all the esters of the inventive compound, of the general formula I, including mono-, di-, tri-, tetra-, penta- and hexa-2-(propylpentanoil) myo-inositol, the salts thereof and all the intermediate compounds formed with the several protecting groups hydroxyl, as well as all the chirality and position isomers. These protective groups are protecting the individual hydroxyls, the neighbor hydroxyls, alternated hydroxyls, 1,2-; 1,3- diols, 1,3,5- such as allyl ethers, chloroacetate ester, 2,2-dimethoxypropane, cyclohexanone, methoxyacetate ester, pivaloate ester, ethylidene acetal, 2,2,2-thrichloroethylidene acetal, acetonide (isopropyliden ketal), 2-methoxypropane, benzylidene acetal, triethyl orthoformiate, phosphates, etc.

The compound of the invention also may be incorporated into a pharmaceutical composition comprising a therapeutically effective amount of valproic acid or pharmaceutically acceptable derivative thereof covalently bonded to an amount of myo-inositol.

The inventive compound is preferably employed in the treatment of a central nervous disorder and may be administered to a subject in need thereof in a therapeutically effective dose. The dose may be an anti-epileptic effective dose, or an anti-convulsive effective dose or an anti-bipolar disorder effective dose.

The compound is basically obtained by mixing a myo-inositol based compound with a valproic acid based compound into a solution, leaving the mixture to react and collecting a reaction product.

This invention will be better understood from the following examples. However, those of ordinary skill in the art will readily understand that the examples are merely illustrative of the invention as defined in the claims which follow thereafter.

EXAMPLE 1

Preparation of (±)1,2,3,4,5,6-hexa-O-(2-propylpentanoyl)-myo-inositol of the formula I:

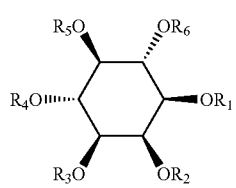

(I)

Wherein: R=2-propylpentanoyl

The mixture of 6 g (0.033 M) of inositol in 120 ml of triethylamine was stirred at room temperature for 30 min, then was added 5 g (0.041M) of 4-(dimethylamine) pyridine and was very slowly added 54 g (0.2M) of 2-propylpentanoic anhydride. After adding all of the anhydride the reaction mixture was stirred at 45° C. for 72 hours and then the solvent was remove under reduce pressure. The mixture was extracted with 200 ml of ethylacetate and the organic phase was washed with water, 5% potassium carbonate and finally water. After drying over anhydrous sodium sulfate the solvent was removed in vacuo. The product was purified by column chromatography on silica gel hexane:dichrometane 2:1, was crystallized from methylenchloride melting at 67-69° C. Yield 43%.

IR (KBr):ν1736 (C=O)

$^1$H NMR (chloroform-$d_3$): δ 0.84, 0.86, 0.89, 0.92, 0.94, 0.96, 0.99 (9 s, 36H, $CH_3$), 1.18-1.68 (m, 48H) 2.16-2.30 (m, 5 CH), 2.32-2.44 (m, 1H), 5.23 (dd, 2H), 5.34 (t, 1H), 5.59 (t, 1H).

$^{13}$C NMR (cloroform-$d_3$): δ 13.94, 13.96, 13.98, 14.04 ($CH_3$), 19.98, 20.20, 20.39, 20.43, 20.47, 20.58 ($CH_2CH_3$) 33.0-35.10 ($CH_2$), 44.30-45.04 (CH), 69.39-74.44 (CH) 173.5-178.04 (COO) values were consistent with the assigned structure.

EXAMPLE 2

Preparation of (±)-5,6-Di-O-(2-propylpentanoyl)-1,2:3,4-di-O-cyclohexyl-O-myo-inositol of the formula II:

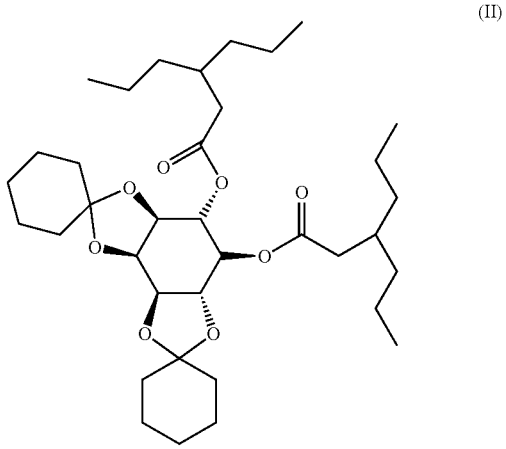

(II)

Alternatively, the compound may be defined in relation to general formula I, wherein $R_1=R_2=$O-cyclohexyl-O and $R_3=R_4=$O-cyclohexyl-O, and $R_5=R_6=$2-propylpentanoyl.

To a stirring suspension of 2.6 g (0.01M) of (±)-1,2:5,6-Di-O-cyclohexyl-O-myo-inositol in 20 ml of dry triethylamine was added 49 mg. (0.004M) 4-(dimethylamino) pyridine and stirred 45 min. 2-Propylpentanoic anhydride 5.7 g (0.021M) was added to the suspension at room temperature. The reaction was stirred at rt for 40 h. and the solvent was removed under reduce pressure. This product was crystallized from MeOH, to give a white crystals melting at 65-66° C.

IR (KBr): ν1740 (C=O).

$^1$H NMR (CDCl3): δ 0.82-0.94 (m, 12H, CH3), 1.25-1.74 (m, 16H, CH2), 1.28, 1.36, 1.44, 1.54 (4 s, 12H, 2C(CH3)2), 2.28-2.45 (m, 2H, CH), 3.42 (dd, J 10.0 J 9.2 Hz, 1 H, H-5), 4.1 (dd, J 10.0, J 8.2 Hz, 1, H-6), 4.28 (dd, J 8.3 Hz, J 6.1 Hz, 1 H, H-1), 4.62 (dd, J 6.1, J 4.6 Hz, 1 H, H-2), 5.08 (dd, J 4.5; J 5.6 Hz, 1 H, H-3), 5.30 (dd, J 9.2, J 5.7 Hz, 1H, H-4)

13C NMR (CDCl3): δ 13.8 (4×CH3), 20.3, 20.5, 20.2, 20.4 (4×CH2CH3), 25.9, 26.8, 27.0, 27.8 (4×CH3), 34.3, 34.42, 34.70 (4×CH2CH2CH3, 1 overlapping), 44.7, 45.1 (2×CH), 71.6, 71.8, 74.2, 76.3, 76.8, 78.8 (6×CH), 111.2, 112.8 [2×C (CH3)2], 174.2, 175.3 (2×COO) Anal. Calcd for C28H48O8: C, 65.6; H, 9.4. Found C, 66.5; H, 9.4.

EXAMPLE 3

Preparation of (±)-3,4,5,6-tetra-O-(2-propylpentanoyl)-1,2-O-isopropylidene-myo-inositol of the formula III:

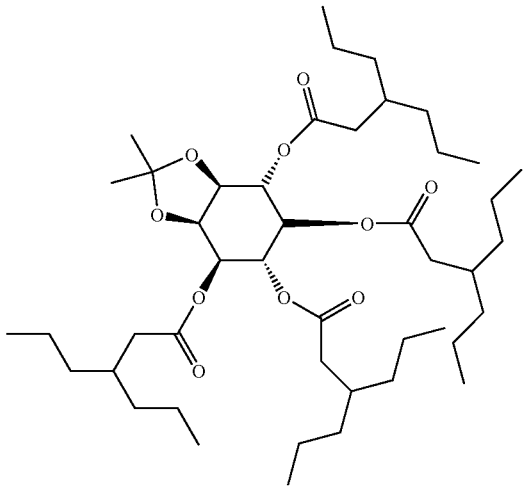

(III)

Alternatively, the compound may be defined in relation to general formula I, wherein $R_1=R_2=$O-isopropyledene and $R_3=R_4=R_5=R_6=$2-propylpentanoyl.

To a stirring suspension of 11 g (0.05M) of (±)-1,2-O-isopropylidene-myo-inositol in 90 ml of dry diethylamine was added 2.44 g (0.02M) of 4-(dimethylamino) pyridine and stirred 30 min. 2-propylpentanoic anhydride 59.4 g (0.22M) was added to the suspension at room temperature. The reaction was stirred at rt for 35 h. and then the solvent was removed under reduce pressure. The crude product was purified by column chromatography on silica gel, using first 2:3 hexane-ethyl acetate and then 3:1 dichloromethane-ethyl acetate as eluentes. Obtained in this manner as a pale yellow viscous oil in 63% yield.

IR: ν1748 (C=O).

$^1$H NMR (DMSO-d$_6$): δ 0.89, 0.90, 091, 0.92, 0.93, 0.94, 0.95, 0.96, 0.97 (8 s, 24H), 1.30-1.60 (m, 32H), 1.61-1.66 (m, 6H), 2.34-2.39 (m, 2H), 2.45-2.48 (m, 2H), 4.42 (dd, 1H), 4.71 (dd, 1H), 5.10 (t, 1H), 5.23 (t, 1H), 5.32 (dd, 1H), 5.52 (dd, 1H).

$^{13}$C NMR (DMSO-d$_6$), values were consistent with the assigned structure.

Anal. Calcd for C$_{41}$H$_{72}$O$_{10}$: C, 67.95; H, 9.97. Found C, 67.92; H, 9.95.

EXAMPLE 4

Preparation of (±)-3,4,5,6-tetra-O-(2-propylpentanoyl)-myo-inositol of the formula IV.

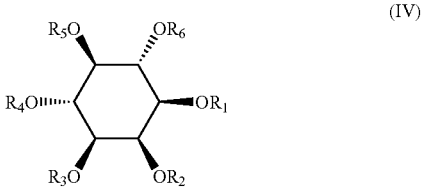

(IV)

Alternatively, the compound may be defined in relation to general formula I, wherein $R_1=R_2=$H, and $R_3=R_4=R_5=R_6=$2-propylpentanoyl, including the different protecting groups, esters and salts derivatives of the myo-inositol with 2-propylpentanoyl.

A mixture of 5 g (0.0) of (±)-3,4,5,6-tetra-O-(2-propylpentanoyl)-1,2-O-isopropylidene-myo-inositol and trifluoracetic acid 15% (Trifluoracetic acid-THF) was stirred at room temperature for 48 hours, then condensed in vacuo. The product was purified by column chromatography on silica gel, using 4:1 hexane-ethyl acetate. The product obtained in this manner was white solid, with a melting point: 89-91° C.

IR and $^1$H, $^{13}$C NMR, or NMR values were consistent with the assigned structure.

EXAMPLE 5

Preparation of (±)-3,4-Di-O-(2-propylpentanoyl)-myo-inositol of formula V.

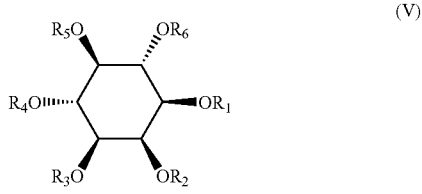

(V)

Alternatively, the compound may be defined in relation to general formula I, wherein $R_1=R_2=R_5=R_6=$H and $R_3=R_4=$2-propylpentanoyl, including the different protecting groups, esters and salts derivatives of the myo-inositol with 2-propylpentanoyl.

A mixture of compound (±)-3,4-Di-O-(2-propylpentanoyl)-1,2:5,6-di-O-isopropylidene-myo-inositol (6 g, 0.012M) and 60 ml of trifluoracetc acid 15% (Trifluoracetic acid-THF) was stirred at room temperature. After 60 Hs the reaction mixture was concentrated in vacuum. The product was purified by column chromatography on silica gel, using (CH2Cl2:MeOH). Obtained a white solid mp: 128-131 (IR (KBr): ν3210-3540 (OH) 1760 cm−1 (C=O).

1H NMR (CDCl3): δ 0.87, 0.90, 0.94 [3 s, 12H, (CH3)4, 1 overlapping], 1.21-1.85 (m, 16H, CH2), 1.28, 1.53 [2 s, 6H, C(CH3)2], 1.95 (br, s, 1H, OH), 2.38-2.58 (m, 2H, CH), 2.99 (br, s, 1H, OH), 3.41 (t, J 9.8 Hz, 1H, H-5), 4.01 (t, J 9.7 Hz, 1H, H-1), 4.11 (dd, J 7.7, J 4.8 Hz, 1 H, H-4), 4.45 (t, J 4.4 Hz, 1 H, H-2), 5.00 (dd, J 10.1, J 4.1 Hz, 1 H, H-3), 5.09 (dd, J 10.4, J 7.7 Hz, 1 H, H-6); 13C NMR (CDCl3): δ 13.9 (valproil 4×CH3), 20.3, 20.4, 20.5 (4×CH2CH3, 1 overlapping), 25.8, 27.7 (2×CH3), 34.5, 34.7 (4×CH2CH2CH3, 2 overlapping), 45.3, 45.4 (2×CH), 70.9, 72.6, 73.6, 75.1, (inositol 6×CH, 2 overlapping), 110.3 [C(CH3)2], 176.4, 177.1 (2×COO). Anal. Calcd for C25H40O8: C, 63.51; H, 9.4. Found C, 59.92; H, 9.05.

Various tests have been carried out employing the above exemplified compounds and a control comprising valproic acid in order to measure several characteristics as shown and described below.

Pharmacological Evaluation

In Vivo Experiments: The pharmacological tests were performed according to standard procedures provided by the Antiepileptic Drug Development (ADD) Program of the National Institute of Neurological and Communicative Disorders and Stroke (NINCDS).

Anticonvulsant tests: Maximal electroshock seizures were elicited in mice by delivering a 60 Hz/50 mA electrical stimulus for 0.2 sec. via ear clip electrodes. A drop of saline solution applied on each ear before placing the electrodes ensures adequate electrical contact. In these conditions, maximal seizures are produced in virtually all normal mice. The maximal seizure typically consists of a short period of tonic flexion followed by a longer period of tonic extension of the hind limbs and a final clonic episode. Blockade of the hind limbs tonic extensor component due to the drug treatment is taken as the end point. The tonic component is considered abolished if the hind leg tonic extension does not exceed a 90° angle with the trunk.

The PTZ test identifies substances that raise the seizure threshold. The freshly made solution of PTZ (1.7% in 0.9% saline solution) is administered subcutaneously (sc) into a loose fold of skin in the midline of the neck in a volume of 5 ml/kg body weight. This amount of PTZ induces convulsions in more than 97% of mice. Animals are observed for at least 30 min after sc injection of PTZ for the presence or absence of a convulsive episode persisting for at least 5 s. Absence of a clonic seizure indicates protection.

Neurotoxicity tests: The RotoRod test is used exclusively in mice to assess minimal neurotoxicity. A normal mouse can maintain its equilibrium on a rotating rod (6 rpm) for long periods of time. Neurological deficit is indicated by failure to keep walking on this rotating rod in each of three trials of 1 min each.

Determination of the Time of Peak Effect (TPE): The test compounds were administered to groups of 3-5 animals each that were tested at different times (usually 30 min, 1 h, 2 h and 4 h, or when the maximum effect has been passed). The percentages of protection or neurotoxicity are recorded and plotted against time and the TPEs are determined by visual inspection of the graphs.

Estimation of the ED50s: Groups of 8 animals per dose are injected via ip. At least 4 doses between those that induce no protection (0% of the animals) and total protection (100% of the animals), were assayed at the TPE determined as previously described. The percentages of protection at each dose (converted to probit) were plotted against log-doses. These data were then subjected to statistical analysis and the ED50s with the 95% confidence intervals, slopes of the regression lines, and standard errors of the slopes were estimated by the method of Litchfield and Wilcoxon.

Estimation of the neurotoxic effects: Groups of 8 animals per dose were injected and tested with the RotoRod test. The percentages of animals showing minimal neurotoxicity were recorded and the higher dose producing neurotoxic effects is reported. TD50 estimations could not be completed due to solubility problems with high doses.

The above commented results are in the following Table 1:

| Compound | TME hours | MES μmol/kg | Rotorod μmol/kg | Relative Power | Protection |
|---|---|---|---|---|---|
| Valproic acid | 0.25 | 1010 | 17% a 1700 | 1 | 1.4 |
| Example 1 | 2 | 100 | 0/6 | | |
| Example 2 | 1 | 80 | 0% 400 | 35 | 12 |
| Example 4 | 1 | 100 | 0% 450 | 9 | 6 |
| Example 5 | 0.5 | 35 | 0% 300 | 35 | 12 |

TME: Time to Maximum Effect.
MES test: Effective doses 50, in micromols per Kg. of mouse weight.
Rotorod Test.
PR: Relative Power in relation to 2-propylpentanoic acid (Valproic acid).
Protection: Rotorot test on Effective Doses 50.

As it is clear from the above listed results the therapeutic activity or power of the inventive compound is higher several times the power of the valproic acid used alone.

While preferred embodiments of the present invention have been illustrated and described, it will be obvious to those skilled in the art that various changes and modifications may be made therein without departing from the scope of the invention as defined in the appended claims.

We claim:

1. A compound of the formula I:

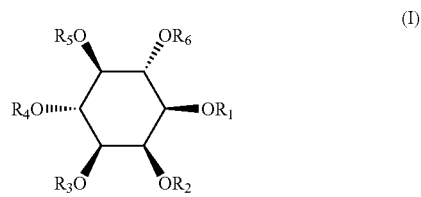

wherein:
$R_1$, $R_2$, $R_3$, $R_4$, $R_5$ and $R_6$ are each independently selected from the group consisting of H; 2-propylpentanoyl; O-cyclohexyl-O; O-isopropylidene and $PO_3H_2$;
with the proviso that at least one of the $R_{1-6}$ groups is a 2-propylpentanoyl group,:
including the position isomers, enantiomers
thereof and excluding (±) 3, 6-di-O-valproyl-myo-inositol.

2. The compound of claim 1, comprising (±) 1, 2, 3, 4, 5, 6-hexa-O-(2-propylpentanoyl) myo-inositol having the formula:

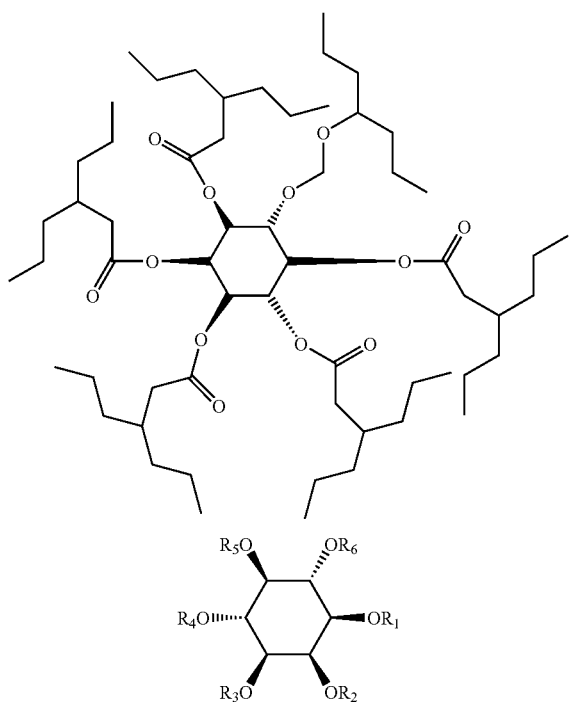

wherein $R_1$ to $R_6$ =2-propylpentanoyl.

3. The compound of claim 1, consisting of (±) 4, 5di-O-(2-propylentanoyl)-myo-inositol having the formula:

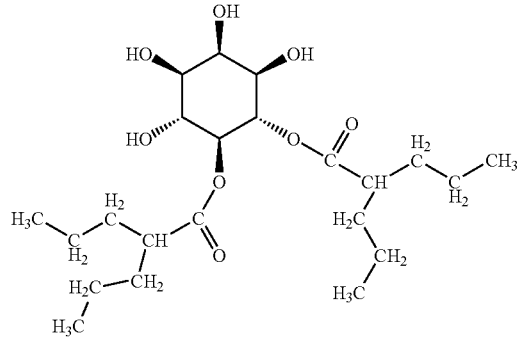

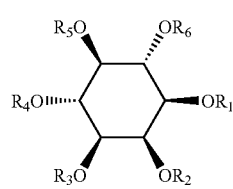

wherein $R_1$, $R_2$, $R_3$ and $R_6$ are H, and $R_4$ and $R_5$ are 2-propylpenanoyl.

4. The compound of claim 1, consisting of (±) 3, 4-Di-O-(2-propylpentanoyl) 1, 2, 5, 6-di-O-isopropylidene-myo-inositol having the formula:

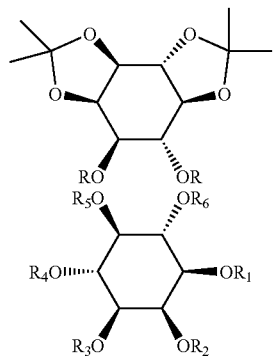

wherein $R_1$, $R_2$, $R_5$ and $R_6$ are H, and $R_3$ and $R_4$ are 2-propylpenanoyl.

5. The compound of claim 1, consisting of (±) 3, 4, 5, 6-tetra-O-(2-propylpentanoyl)-1, 2-O-isopropylidene-myo-inositol having the formula:

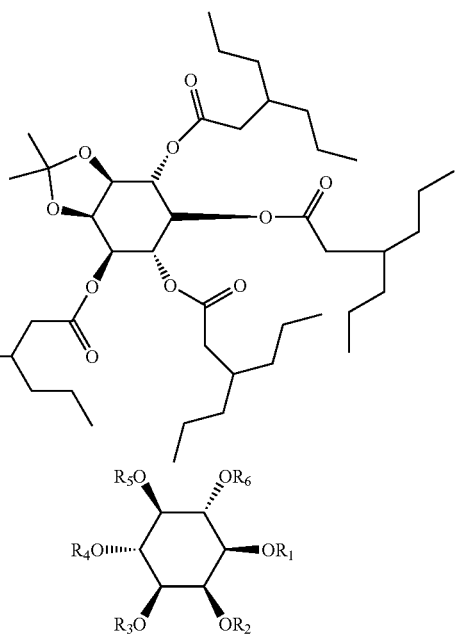

wherein $R_1$, and $R_2$ are H, and $R_3$, $R_4$, $R_5$ and $R_6$ are 2-propylpenanoyl.

6. A pharmaceutical composition comprising a therapeutically effective amount of a compound according to claim 1 and a pharmaceutically acceptable carrier.

7. The pharmaceutical composition of claim 6, for treating a central nervous disorder in a subject, wherein the therapeutically effective amount of the compound is an anti-epileptic effective amount.

8. The pharmaceutical composition of claim 6, wherein the therapeutically effective amount of the compound is an anti-migraine effective amount.

9. The pharmaceutical composition of claim 6, wherein the therapeutically effective amount of the compound is an anti-bipolar disorder effective amount.

* * * * *